(12) United States Patent
Abbott et al.

(10) Patent No.: US 7,369,240 B1
(45) Date of Patent: May 6, 2008

(54) APPARATUS AND METHODS FOR REAL-TIME ADAPTIVE INSPECTION FOR GLASS PRODUCTION

(75) Inventors: Mark Matthew Abbott, Dundas, MN (US); Douglas Phillip Wornson, Northfield, MN (US); Eric Loren Hegstrom, Tucson, AZ (US)

(73) Assignee: Litesentry Corporation, Dundas, MN (US)

( * ) Notice: Subject to any disclaimer, the term of this patent is extended or adjusted under 35 U.S.C. 154(b) by 32 days.

(21) Appl. No.: 11/459,015

(22) Filed: Jul. 20, 2006

(51) Int. Cl.
*G01N 21/84* (2006.01)

(52) U.S. Cl. ........................ 356/429; 356/430
(58) Field of Classification Search ........... None
See application file for complete search history.

(56) References Cited

U.S. PATENT DOCUMENTS

| | | | |
|---|---|---|---|
| 4,223,346 A | 9/1980 | Neiheisel | |
| 4,492,477 A | 1/1985 | Leser | |
| 4,812,740 A | 3/1989 | Shutts | |
| 5,132,631 A * | 7/1992 | Klopfenstein et al. | 324/676 |
| 5,598,262 A | 1/1997 | Jutard | |
| 5,642,198 A | 6/1997 | Long | |
| 5,760,907 A | 6/1998 | Basler | |
| 5,887,077 A | 3/1999 | Bongardt | |
| 6,166,393 A | 12/2000 | Paul | |
| 6,275,286 B1 | 8/2001 | Haubold | |
| 6,359,686 B1 | 3/2002 | Ariglio | |
| 6,437,357 B1 | 8/2002 | Weiss | |
| 6,570,651 B1 | 5/2003 | Haubold | |
| 6,683,695 B1 | 1/2004 | Simpson | |
| 6,704,441 B1 | 3/2004 | Inaguki | |
| 6,985,231 B2 | 1/2006 | Redner | |
| 7,184,146 B2 | 2/2007 | Trpkovski | |
| 2003/0024180 A1* | 2/2003 | Hartig et al. | 52/204.5 |
| 2004/0207839 A1 | 10/2004 | Gerstner | |
| 2007/0103686 A1* | 5/2007 | Tornkvist et al. | 356/417 |

FOREIGN PATENT DOCUMENTS

| | | |
|---|---|---|
| WO | WO2005/073698 A1 | 8/2005 |
| WO | WO2005/121699 A1 | 12/2005 |

* cited by examiner

*Primary Examiner*—Michael Stafira
(74) *Attorney, Agent, or Firm*—Edward A. Weck

(57) ABSTRACT

An apparatus and methods for the real-time inspection for defects in and on transparent sheets, such as a sheet of glass, are described. A sensor detects a transparent light reflective coating on a transparent sheet and defines a sample profile. An optical inspection system utilizes an illumination source and an imaging device to obtain images of the transparent sheets. An image processing system analyzes for defects in the transparent sheets, including coating defects and defects in edge deleted perimeters. Inspection variables which correspond to the sample profile are used by the optical inspection system and image processing system for real-time inspection.

21 Claims, 5 Drawing Sheets

APPARATUS AND METHODS FOR REAL-TIME ADAPTIVE INSPECTION FOR GLASS PRODUCTION

BACKGROUND OF THE INVENTION

1. Field of the Invention

The present inventions relate to an inspection system for glass sheet material and, more particularly, consecutive inspection for defects in coated and non-coated glass.

2. Description of the Related Art

During the manufacture of transparent materials, optical defects and deviations may be produced that render the transparent material imperfect. Optical imperfections are of special concern in glass and plastic sheet applications where optical defects are unacceptable from a quality control standpoint. Optical quality defects include surface imperfections, inclusions and inconsistencies in light transmission or reflection. Scratches, digs, coating anomalies, seeds, stones, chips, particles, tin residue, ripples, distortion, and grind lines are common categories of optical quality defects.

Insulated glass (IG) units used in the manufacture of windows are made of two sheets of glass sealed together with a spacer between the two sheets of glass. One sheet of glass is often coated with a thin-film low emissivity (low-E) coating prior to assembly of the IG unit. The low-E coating improves the insulating value of the window by reflecting much of the infrared (IR) and heat-carrying portion of the spectrum. Windows manufactured with low-E coatings typically cost about 10-15% more than IG units made with uncoated glass, but they reduce energy loss through the window by as much as 30-50%.

IG units are manufactured in many ways, ranging from manual assembly to highly automated assembly with little or no human handling. Automated IG unit assembly involves loading two matching glass sheets in sequence onto an assembly line. A typical IG unit consists of one clear sheet of glass and one low-E coated sheet of glass, although other variations are possible such as two clear sheets of glass. After the two glass sheets are loaded onto the assembly line, the low-E coated glass sheet is "edge-deleted" whereby about 0.375 inch of the coating is removed from the perimeter of the glass sheet by grinding. Removal of the coating is necessary to avoid corrosion of the low-E coated glass after assembly into an IG unit. Edge deletion is described in more detail in US Patent Application No. 2003/0024180 A1. The proper geometry for the edge deletion is typically a uniform band measuring 0.375 inches in width from the edge of the glass. After the low-E glass has the coating removed from the edge, the glass sheets are washed, inspected, a spacer with sealing material is applied, the unit is pressed together, trapped air may be removed and a low-conductivity gas such as Argon may be added, and a secondary seal is applied.

Optical inspection of the glass sheets prior to assembly into an IG unit is highly desirable. Once a defective sheet of glass is assembled into an IG unit, the entire IG unit is deemed defective and must be discarded. An IG unit is valued at approximately ten times the value of a single glass sheet. Optical inspection by humans is inconsistent, subject to high error rates and expensive. Automation of the optical inspection process is highly desirable.

A fundamental problem with automated optical inspection relates to the variance in the optical properties of clear glass as compared to coated glass. The application of multi-layer, optical thin-films coatings to glass results in changes in color, reflection and transmission of light as compared to clear glass. A wide variety of thin film coatings are produced for the window industry, including many types of low-E coatings. The various coatings offer variety in color, reflection, transmission and solar control properties. The proper and accurate optical inspection of glass sheets necessitates unique configuration of the automated optical inspection system appropriate for the type of glass and coating being inspected. Unique configurations include specific lighting arrangements, camera settings such as aperture and shutter speed, and unique inspection variables within the logic governing the automated inspection.

The optical quality of flat glass used in IG units, can be determined through the use a digital imaging device arranged to inspect the glass. This inspection could be done using illumination that reflects off the glass or transmits through the glass. The focus of the digital imaging device is on the glass sheet and the camera generates signals revealing the quality of the glass.

The use of artificial vision for the automated inspection of transparent materials and glass in particular is currently limited by a lack of effectiveness for the detection of imperfections in and on coated and uncoated glass on the same production line.

SUMMARY OF THE INVENTION

Apparatus and methods in accordance with the present inventions may resolve many of the needs and shortcomings discussed above and will provide additional improvements and advantages as will be recognized by those skilled in the art upon review of the present disclosure.

DEFINITIONS

"Inspection variables" are defined to include a) "camera settings" b) "analysis settings" and c) "lighting settings."

"Camera settings" relate to the camera and include aperture, shutter speed, brightness, gain, sensitivity, offset, gamma compensation, filter selection (color or polarization) and camera selection.

"Analysis settings" include sensitivity, offset, intensity thresholds, size thresholds, shape threshold, contrast, filter settings, texture thresholds and logic sequences. Methods used may include intensity thresholding, either absolute or adaptive. Filters may be used prior to thresholding in order to remove unwanted information or to enhance certain types of features. Shapes of anomalies appear in the image as white "blobs" on a dark background. Standard blob analysis may be used to generate many types of measurements on the blobs including, for example length, width, ratio of perimeter to area and Euler number. The definition of particular defects is a matter of defining ranges or combinations of ranges in these numbers which indicate the presence of that particular defect.

"Lighting settings" include light levels (intensity), selection of specific lights, and polarization or color filters.

The "sample profile" is a set of characteristics and their measured values. These values are measured by the sensor. The sample profile is specific to each glass sheet. The sample profile is set in the embedded microprocessor and transmitted to the image processing system.

An "edge delete" is the removal of the coating from the perimeter of the glass sheet by grinding. Removal of the coating is necessary to avoid corrosion of the low-E coated glass after assembly into an IG unit.

An "edge delete perimeter" is the about 0.375 inch wide band of coating removed from the perimeter of the glass sheet by grinding.

The "optical inspection system" is defined as the illumination system combined with the imaging device, most commonly a camera and the image processing system.

The glass defect detection system according to this invention may be used to inspect optically transparent sheets of various kinds including glass, coated glass, mirrored glass, acrylic, polycarbonate, and other optically transparent or transmissive polymer sheets. Other optically transparent or optically transmissive (high transmission) polymer sheets include, and are not limited to, polypropylene and polyethylene.

A glass defect detection system according to this invention may analyze glass while being moved on a conveyance system in a production process. The glass moving on the conveyance system may be of the various widths used in commercial glass production. The conveyance system for moving glass may be oriented vertically or horizontally. The conveyance system may employ a belt or rollers or donuts for moving the transparent sheets. The conveyance system may employ an air float system to move the transparent sheets. The conveyance system may be operable at speeds up to 2 m/sec or higher. The conveyance system may transport glass of widths up to 3 m in width, and from 0.5 mm to 19 mm in thickness. Window-sized pieces of glass may be generally 1 to 2 square meters in size and be transported by the conveyance system.

A glass defect detection system in accordance with the present invention may provide an encoding device. The encoding device may be a digital electronic device used to convert the angular position of a shaft or axle to a digital code, making it a sort of transducer. The encoding device may measure the rate of movement, the acceleration and the deceleration of the conveyance system. The encoding device makes real-time measurements of the incremental movement of the glass sheet. The encoding device transmits the information about the position of the conveyance system to the trigger circuit.

Glass defect detection systems in accordance with the present invention may provide a trigger circuit. The trigger circuit transmits information about the position of the conveyance system to a plurality of cameras. The trigger circuit triggers the cameras to take an image at specific intervals which relate to the precise position of the glass sheet on the conveyance system.

A glass defect detection systems in accordance with the present invention may provide sensors for detecting the presence or absence of a coating on a glass sheet moving on a conveyance system in a glass production process. Various types of sensors may be used for the detection of coatings on glass sheets or transparent materials. These sensors may use laser light, collimated light, semi-collimated light, colored light, or light of a specific wavelength reflected from or transmitted through the coated glass.

The coating sensor may use a photodiode receiver and an LED emitter which provides light as a light source. The sensor may use a concentrated light source that projects light. The light source may be aligned to direct the light at the glass at a predetermined angle for example, at about 5 degrees. The coating sensor may utilize: the reflection of infrared light of 940 nm, the reflection of a combination of ultraviolet light of 200 to 320 nm and infrared light 850 to 950 nm; or the reflection of discrete wavelengths in the range 200 nm to 2000 nm that are unique to low emissivity glass. The sensor may use a lens to focus the light beam. The sensors may include various commercially available light beam detectors. Additional devices for the detection of a coating on a glass sheet are described in the art, such as U.S. Pat. Nos. 6,683,695 and 5,887,077 and are hereby incorporated by reference.

A defect detection system in accordance with the present invention may provide an illumination system for detecting defects on transparent media. It is known to be difficult to detect defects on coated low-E glass and uncoated glass with a single lighting scheme. A combination of lighting schemes may be used to detect defects on the coated portion of glass, the edge of the glass where the coating is removed, and on uncoated glass. The combination of lighting may include a bright field light source and a dark field light source. The light may be directed at the glass at various angles, wavelengths and intensities. The light may be disperse, diffuse, semi-collimated or coherent and monochromatic. Light sources may include fluorescent, strobe, LED, incandescent and laser light.

The bright field light is a homogeneous broad diffuse light or area light, in which reflected images of the light source are in the field of view of the camera. Bright field illumination may be used to detect defects on the glass sheet including coating defects and edge deletion skips. Bright field illumination may be used for shape recognition, size recognition, and edge definition. Bright field illumination may be realized by a variety of means including LED, fluorescent, incandescent, strobe, and laser light. The wavelength of the LED lights are selected to match the wavelength sensitivity of the camera.

Features on the glass which involve changes in reflectivity or diffusion can be observed in the bright-field. Some of these involve non-uniform coating and some involve textures on the glass. Since the purpose of most coatings applied to glass is to change the reflectivity or transmission at particular wavelengths, or to change the diffusion of reflected light, the detection and quantification of non-uniformities in the coating is useful for quality control during the application of coatings. Further, it becomes possible to monitor the results of deliberate removal of coatings, as is often done at the edges of coated glass sheets prior to assembly into IG units.

Dark field lighting consists of darkening the center of the field of view of the camera so that no light rays penetrate directly into the camera. Reflected images are out of the field of view of the camera. Conventional dark-field illumination involves propagating light at the glass sheet at a glancing angle to the surface of the glass sheet. Said glancing angle varies from 5 degrees to 90 degrees (normal) to the glass sheet, depending on the manufacturer of the imaging system. In dark field illumination, only light scattered from the feature or defect is detected by the camera.

The dark-field light sources may be high-intensity LED's, each of whose light is shaped by a lens into a narrow, semi-collimated beam. The LED's and lenses may be assembled side by side into densely packed lines and attached to fixturing bars. Dark field illumination may be realized by a variety of means including LED, fluorescent, incandescent, strobe, and laser light.

A glass defect detection system in accordance with the present invention may provide an imaging device or camera for the visualization of defects on a transparent medium such as a glass sheet. The camera may be an electronic imager based on a grid of areas, an electronic area-based detector. The illumination of the glass sheet may be detected by a CCD (charge coupled device) image sensor. Other image detection sensors may also be used, such as a CMOS (complementary metal oxide semiconductor) image sensor or other image sensors. Line scan cameras may also be used as image detection devices in accordance with the present invention. The "camera settings" for the camera may be adjusted or altered to examine defects in different types of glass including glass with various types of coatings.

The field of view of the camera may be divided, with approximately half of the field of view containing dark field light and half of the field of view containing bright field light. The bright field light is a single uniform, diffuse area light. The light is positioned so that when the camera observes it in reflection off the glass, it appears in only half the image. The glass entry region into the camera field of view may be the bright field and the glass exit regions from the camera field of view may be the dark field. The bright field examination of glass is suitable for shape recognition, size recognition, edge definition, coating defects, edge deletion skips, inclusion defects such as seed and stones and repetitive defects of a similar nature. The dark field examination is suitable for scratches, digs, surface blemishes, edge chips, edge deletion, inclusion defects and repetitive defects of a similar nature.

A glass defect detection system in accordance with the present invention may provide an image processing system for the detection and visualization of defects on a glass sheet. The image processing system receives a signal from the coating sensor indicating whether the glass is coated or uncoated. If the glass is coated, the image processing system also receives a signal indicating the characteristics of the coating. The image processing system may generate binarized images from the cameras which are processed to determine the location, type and magnitude of defects in or on the sheet of glass. The output from the image processing system may be displayed on a display device. A plurality of high-speed commercial processors may be used in the defect detection system for image processing.

The present invention has been designed to produce images in which, when there is glass present, the appearance of the glass is extremely uniform, black in the dark-field and middle-gray in the bright field. The detection of defects begins with finding of anomalies in this uniformity. Standard image processing techniques may be used to characterize and ultimately to classify the nonuniformities as particular types and sizes of defects or as non-objectionable anomalies (for example, dust). These techniques generally involve producing a binarized image, and are commonly called blob analysis.

A glass defect detection system in accordance with the present invention may provide adjustable inspection variables for examining defects in a glass sheet. The inspection variables may be adjusted differently for uncoated glass and for coated glass. The defect detection system can be adjusted or altered to examine defects in different types of glass including various types of coatings on the glass. The inspection variables may adjusted for shape requirements, thresholds for defects (geometric characteristics such as edge deletes can be measured by looking at changes in contrast and absolute brightness), image processing parameters, and descriptions of norms for a variety of types of glass under analysis. The inspection variables allow the ability to distinguish between various types of low emissivity coatings. The inspection variables for coated and non-coated glass may be changed instantaneously so that an automated IG unit assembly line operates in an uninterrupted manner.

A glass defect detection system in accordance with the present invention may provide an image display. The image processing system receives a signal from the cameras which it processes. The information from the cameras processed by the image processing system may be displayed on an image display. Alternatively an automated device could discard defective glass sheets.

A glass defect detection system in accordance with the present inventions may provide an automatic stop and manual restart button. The image processing system of the present inventions may be connected to a start-stop control for the conveyor to allow the conveyor to be automatically stopped by the optical inspection system upon recognition of a defect causing the glass to be rejected. A human operator may examine the actual defect as compared to representation of the defect displayed on the screen, and then make a final judgment on the glass sheet. The restart button commences production and logs the result, either acceptance of the sited reject or rejection of the glass sheet to a database.

The image processing system automatically stops the glass in front of the human operator if a defect in the glass or the glass coating has been detected. The operator need not be present to evaluate the "acceptable" good sheets of glass. Only if the glass has been rejected by the computer defect detection system is an operator decision required before acceptance or rejection of the inspected sheet of glass.

The problem of inspecting both coated glass and clear class is solved by this invention which inspects the class to determine the presence and type of coating prior to automated optical inspection, thereby providing a novel method to adjust the optical system and inspection variables appropriately for the glass to be inspected.

The proper and accurate optical inspection of glass sheets necessitates a unique configuration of the optical system, including lighting and cameras, and unique inspection variables dependent on whether the glass is clear or coated. This problem is solved by this novel new invention which inspects the glass to determine the presence and characteristics of a coating prior to automated optical inspection, thereby providing a novel method to preset the optical system and inspection variables appropriately for the glass to be inspected. That is, the inspection system is automatically adjusted using feed-forward information from a coating sensor.

Other features and advantages of the invention will become apparent from the following detailed description, and from the claims.

BRIEF DESCRIPTION OF THE DRAWINGS

All Figures are illustrated for ease of explanation of the basic teachings of the present invention only; the extensions of the Figures with respect to number, position, relationship and dimensions of the parts to form the preferred embodiment will be explained or will be within the skill of the art after the following description has been read and understood. Further, the exact dimensions and dimensional proportions to conform to specific force, weight, strength, and similar requirements will likewise be within the skill of the art after the following description has been read and understood.

Where used in various Figures of the drawings, the same numerals designate the same or similar parts. Furthermore, when the terms "top," "bottom," "right," "left," "forward," "rear," "first," "second," "inside," "outside," and similar terms are used, the terms should be understood to reference only the structure shown in the drawings and utilized only to facilitate describing the illustrated embodiments.

DETAILED DESCRIPTION OF THE INVENTION

Figure 1:
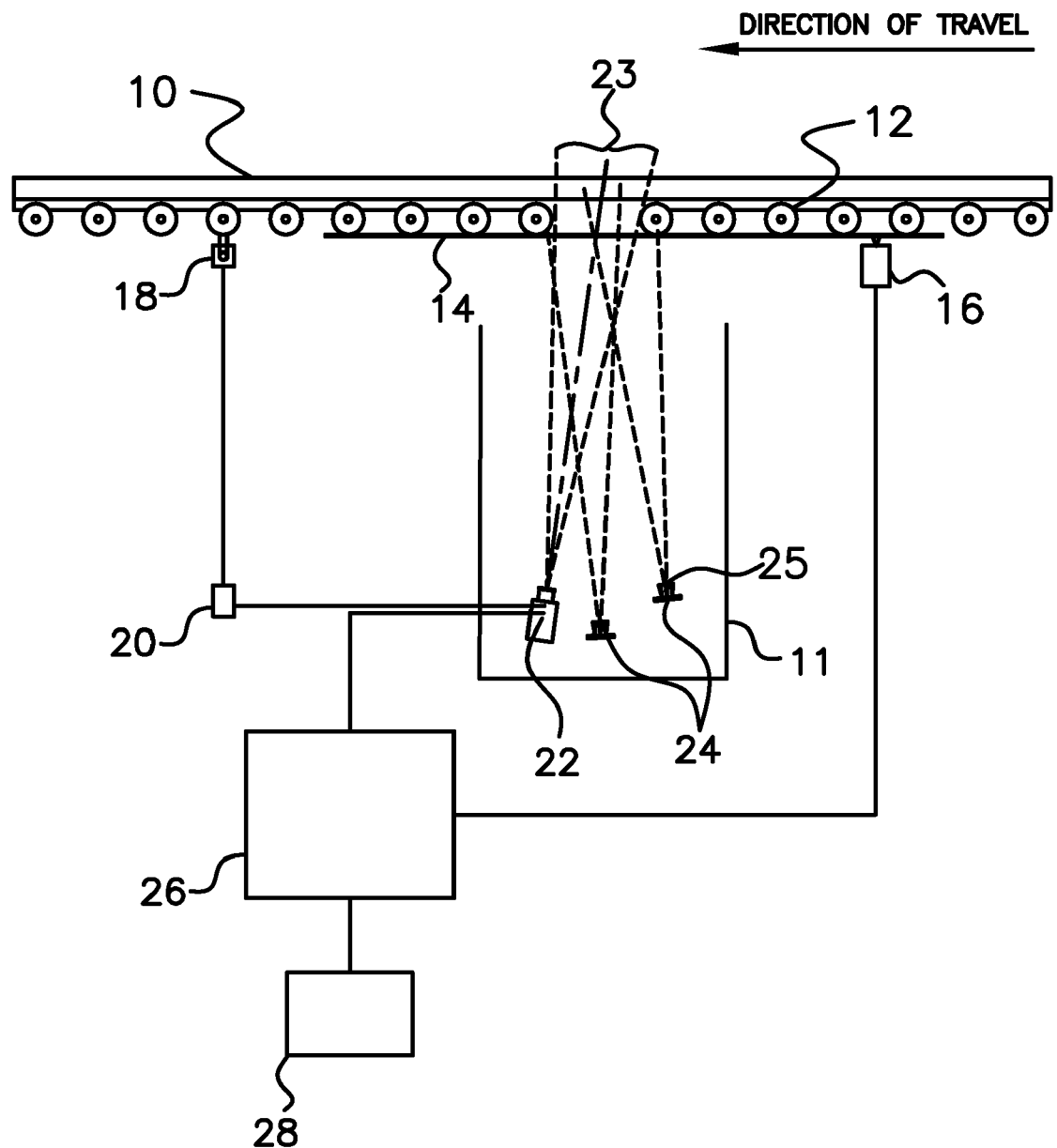
FIG. 1 shows a schematic of a top view of the functional components of the invention.

The figures generally illustrate exemplary embodiments of glass defect detection systems 10 or components thereof which include aspects of the present inventions. The particular embodiments of the glass defect detection system 10 illustrated in the figures have been chosen for ease of explanation and understanding of various aspects of the present inventions. These illustrated embodiments are not meant to limit the scope of coverage but instead to assist in understanding the context of the language used in this specification and the appended claims.

The present inventions provide glass defect detection systems 10 and methods for detecting defects in and on transparent sheets using glass defect detection systems 10. The glass defect detection systems 10 in accordance with the present inventions may permit the analysis of coated glass and non-coated glass on the same glass production line. The glass defect detection systems 10 may be used in the analysis of transparent materials such as acrylic. The glass defect detection systems 10 may be integrated into vertical and horizontal production lines for transparent materials. The glass defect detections systems 10 are configured to analyze defects in and on glass sheets 14.

As illustrated throughout the figures, glass defect detection systems 10 generally include a sensor 16, an encoding device 18, a trigger circuit 20, a camera 22, an illumination system 24 and an image processing system 26. The glass defect detection systems 10 may also include a conveyance system 12, an image display 28 and a housing 11. The glass defect detection systems 10 may include a plurality of cameras 22 and a plurality of illumination systems 24. The glass defect detection systems 10 may also include an interface to the conveyance system 12. The conveyance system 12 typically transports a glass sheet 14 which passes between the conveyance system 12 and a sensor 16. The sensor 16 analyzes reflected light at discrete wavelengths and transmits to the image processing system 26 the type of glass entering the optical inspection. The sensor 16 may also analyze transmitted light. The image processing system 26 adjusts the inspection variables depending on type of coating 15, if any, present on the glass sheet 14 as measured by the sensor 16 just prior to the glass sheet 14 passing in front of the cameras 22 for inspection. To inspect for defects in or on the glass sheet 14, it may be illuminated with a plurality of beams of light in the field of view 23 of the cameras 22 by the illumination system 24. The encoding device 18 transmits an encoding device signal to the trigger circuit 20 which transmits a trigger circuit signal to the cameras 22 to transmit a signal from the cameras 22 to the image processing system 26. The image processing system 26 applies inspection variables to the camera signal and transmits an image output signal to the image display 28.

The conveyance system 12 is generally for transporting glass sheets 14 in a commercial glass production line. The conveyance system 12 may use a belt 13 which turns around rollers on which the bottom edge surface of the glass sheet 14 is conveyed in a manufacturing process. The conveyance system 12 may be like those manufactured by Bystronics or Lisec. Conveyance systems 12 generally known in the art may also be used with these inventions.

Figure 4:
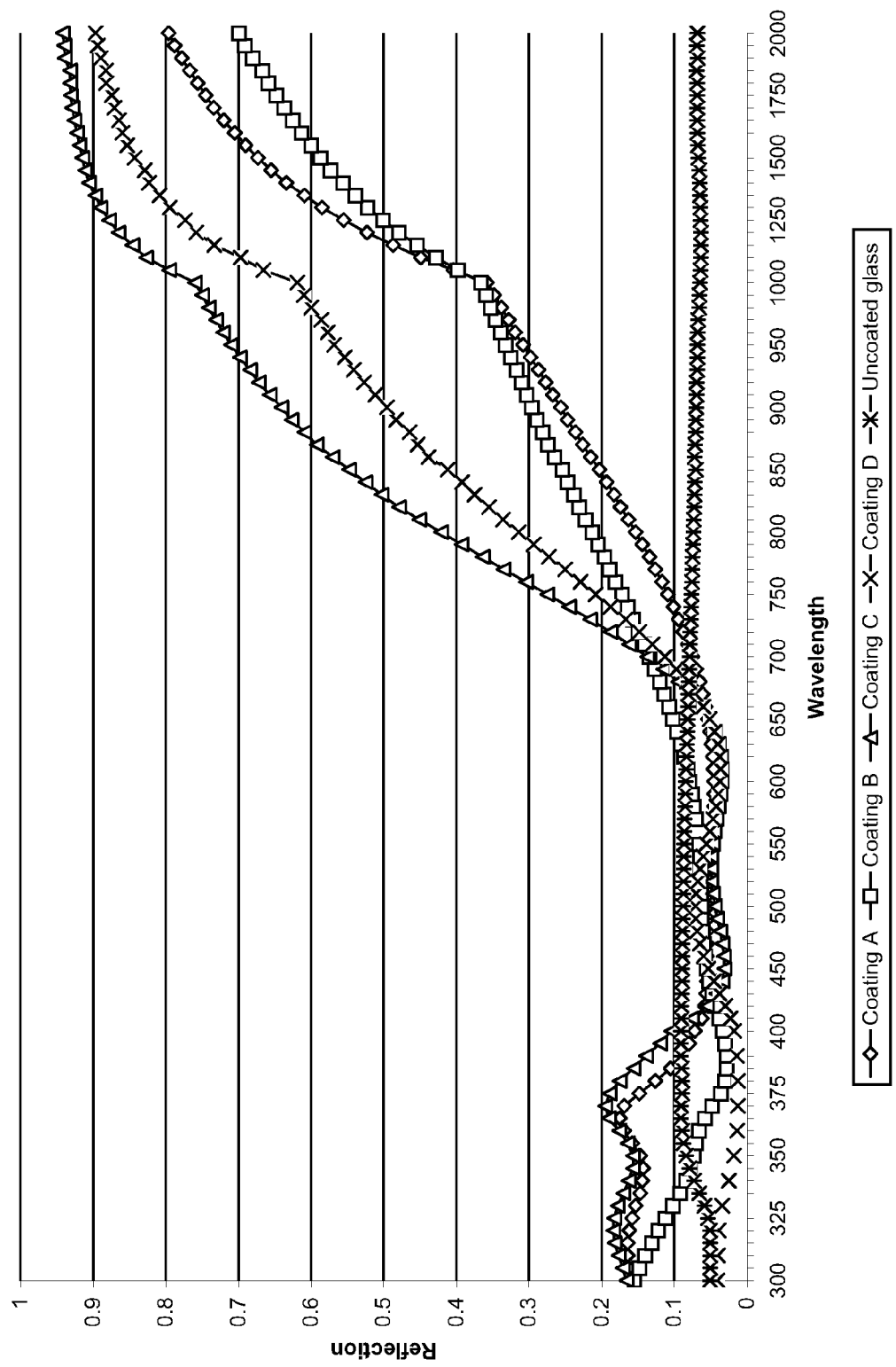
FIG. 4 shows a graph of the optical response of clear and coated glass in reflection over the UV, visible and IR spectrum.

The sensor 16 generally comprises an emitter 30 and a receiver 32. A matched pair consisting of the emitter 30, which may be an infrared-emitting LED, and the receiver 32, which may be an infrared-sensitive photodiode, are selected for light bandwidth in which the glass sheet 14 under test is known to be reflective. The emitter 30 may project light of various wavelengths onto a glass sheet 14. The receiver 32 detects the light. This wavelength of the light may be 940 nanometers. Alternative wavelength pairs of the emitter 30 and the receiver 32 may be used to differentiate between various coated glasses. Wavelengths in the near IR (800 to 1200) and the near ultraviolet (200-320 nm) ranges may be used. FIG. 4 shows the reflection at various wavelengths from uncoated glass and four typical low-E coated glasses. Wavelengths at which a discernable difference in reflection is evident are candidate wavelengths for sensing, such as 360 nm in the UV and 940 nm in the IR.

A signal is generated by pulsing the emitter 30. A lens 34 may be used to focus the light from the emitter 30 on the glass sheet 14. The 940 nm light beam from the emitter 30 passes through the lens 34 and is directed at an angle to the glass sheet 14. Light that reflects from the glass sheet 14 reflects back at the same angle as it arrived at the glass sheet 14. About 7% of a light beam is reflected by the surface of a glass sheet 14 made of non-coated glass while from 30-70% of a light beam is reflected from a glass sheet 14 coated with low-E thin films, as shown in FIG. 4.

In the case of a non-reflective sample, a higher proportion of the IR energy from the emitter 30 transmits through and/or absorbs within the glass sheet 14 and is effectively lost. In the case of lowE or other coated glass, the IR signal is optically coupled from the emitter 30 to the receiver 32 by reflection off the infrared-reflective thin film or coating 15. The IR energy received by the photodiode receiver 32 is filtered via a bandpass filter 36 to remove ambient IR noise, leaving the signal portion. The signal is converted analog-to-digital, and passed to the embedded microprocessor 38 which compares it to threshold values, that have been established empirically by measurement, for the absence of glass, uncoated glass, and various coated glasses. The sensor 16 thereby inspects each glass sheet 14 for the presence of a coating 15, and if present, the type of coating 15 present. The embedded microprocessor 38 transmits a signal to the image processing system 26, the sample profile, indicating the type of glass present, either uncoated or one of a variety of coated glasses.

The encoding device 18 allows the precise tracking of the location of the glass sheets 14 along the conveyance system 12. The encoding device 18 may be a rotary encoder which pulses 2540 times per revolution of a shaft driving the belt 13 of the conveyance system 12. The encoding device 18 may be like those manufactured by Dynapar. The encoding device 18 tracks the position of the glass sheet 14. The encoding device transmits a signal to the trigger circuit 20.

The trigger circuit 20 receives a signal from the encoding device 18 and triggers the optical inspection system by transmitting a signal to the cameras 22. The trigger circuit 20 may trigger the camera 22 to capture an image every 83.4 mm of movement of the conveyance system 12 or every 387 pixels in the field of view of the camera 22. The trigger circuit 20 may trigger the camera 22 at various length interval or pixel dimensions to vary the fields of view of cameras 22.

The illumination system 24 directs light at the glass sheet 14 for the detection of defects in and on the glass sheet 14. The illumination system 24 may provide constant illumination from a plurality of lights. The illumination system 24 may use various lights including incandescent, fluorescent, strobe, laser, or narrow bandwidth LEDs. Lumiled LED lights cyan in color (460-540 nm wavelength) may be used. The wavelength of the LED lights is selected to match the wavelength sensitivity of the camera 22. A lens 25 may shape the light beam from the high-intensity LEDs of the illumination system 24 into a narrow, 10-degree semi-collimated beam.

The camera 22 records an image of the glass sheet 14 as it passes through the light produced by the illumination system 24. The camera 22 receives an input signal from the trigger circuit 20 signalling the camera when to capture an image. The camera 22 may be an area scan image device or line scan image device, either utilizing CMOS image sensors or CCD image sensors. There may be a plurality of cameras 22 recording images of glass sheets 14 as the glass sheets 14 move along the conveyance system 12. The camera 22 takes multiple images and transmits these images to the image processing system 26. The image processing system 26 combines multiple images from the cameras 22 to create a single composite image of the glass sheet 14 as it is passing by the cameras 22. The camera 22 may be an area scan camera manufactured by Point Gray Research with a field of view of 1600×1200 pixels. Other cameras 22 such as area scan cameras and line scan cameras known to those of skill in the art may be used with the present inventions. The "camera settings" for the camera 22 may be adjusted or altered to examine defects on or in different types of glass sheets 14 including glass sheets 14 with various types of coatings 15.

The field of view of the camera 22 may be divided into two areas, which may be equal in area. The first area of the field of view 23 contains dark field lighting and the second area of the field of view 23 contains bright field lighting. The bright field light is a single uniform, diffuse area light. LED lights are used to illuminate a white acrylic sheet which diffuses light over the glass sheet 14 as it passes through the field of view 23. Conventional bright-field illumination involves propagating light substantially normal to a first surface of the glass sheets 14 and collecting into the lens 25 and camera 22, all or virtually all of the light transmitted through or reflected from the illuminated areas of the glass sheet 14. The light is positioned so that when the camera 22 observes the reflection off the glass sheet 14, the bright-field reflection appears in only half the image. Features on the glass sheet 14 which involve changes in reflectivity or diffusion can be observed in the bright field. Some of these involve non-uniform coating 15 and some involve textures on the glass sheet 14.

The dark-field light is comprised of a plurality of LED lights. Conventional dark-field illumination involves propagating light at the glass sheet 14 at a glancing angle to the surface of the glass sheet 14. Said glancing angle varies from 5 degrees to 90 degrees (normal) to the glass sheet 14, depending on the manufacturer of the imaging system. In dark field illumination, only light scattered from the feature or defect is detected by the camera 22.

Since the purpose of most coatings 15 applied to glass sheets 14 is to change the reflectivity or transmission at particular wavelengths, or to change the diffusion of reflected light, the detection and quantification of non-uniformities in the coating 15 is useful for quality control during the application of coatings 15. By the same token it becomes possible to monitor the results of deliberate removal of coatings 15 or the presence of an edge deleted perimeter 19, as is often done at the edges of a glass sheet 14 prior to assembly into a multi-pane insulated glass unit.

The camera 22 and the illumination system 24 are enclosed in a housing 11. The housing 11 reduces the amount of stray light that may be directed at the glass sheet 14 from the room during the inspection process. The housing 11 also provides physical protection from other elements in the production environment.

The image processing system 26 receives and processes signals from the sensor 16 and receives and processes signals from the camera 22. The image processing system 26 comprises a plurality of microprocessors of the Intel Xeon type. The image processing system 26 receives the output from the sensor 16 indicating the presence or absence of coating, and, if coated, the type of coating on the glass sheet 14. Based on the output signal from the sensor 16, the sample profile, the image processing system 26 adjusts the camera settings for the camera 22. If the sample profile from the sensor 16 indicates that the glass sheet 14 is uncoated, the image processing system 26 transmits a signal to the camera 22 to set the shutter speed to be 0.0007 seconds and signal gain to be −3.0 dB and gamma to be 3.5. If the sample profile from the sensor 16 indicates that the glass sheet 14 is coated, the image processing system 26 transmits a signal to the camera 22 to set the shutter speed to be 0.0008 seconds and the signal gain to be 1.5 dB and gamma to be 1.0. The image processing system 26 also receives a signal or image from the camera 22. The image includes both a dark field of view and a bright field of view.

Inspection variables within the image processing system 26 are adjusted according to the signal received from the sensor 16, the sample profile. The signal from the camera 22 is analyzed at different levels of contrast based on the signal received from the sensor 16 which changes the sensitivity of defect detection in and on glass sheets 14. Standard image processing techniques may be used to characterize and classify the non-uniformities as particular types and sizes of defects or as non-objectionable anomalies (for example, dust). Standard image processing techniques are embodied in software available, for example, from Open Source Computer Vision Library, Matrox MIL or Cognex Vision Pro. Image processing techniques generally involve producing a binarized image. Methods used for image processing may include intensity thresholding, either absolute or adaptive. Filters may be used prior to thresholding in order to remove unwanted information or to enhance certain types of features. Shapes of anomalies appear in the image as white "blobs" on a dark background. Standard blob analysis may be used to generate many types of measurements, both individual and composite, on the blobs including, for example, length, width, ratio of perimeter to area, Euler number and blobs per square inch. Ranges or combinations of ranges of these measurements may be defined to indicate the presence of a particular defect.

Inspection variables within the defect detection system 10 can be adjusted or altered to examine defects in different types of glass sheets 14 including various types of coatings 15 on the glass sheet 14. The defect detection system 10 adjustable inspection variables may include shape requirements, geometric analysis of defects, quality thresholds for defects, contrast, absolute brightness, image processing parameters, and descriptions of norms for a variety of types of glass under analysis. The results from image analysis in the image processing system 26 are displayed on an image display 28 so that the user can decide to accept or reject the glass sheet 14. Alternatively an automated device could discard defect glass sheets 14.

FIG. 1 illustrates a schematic of glass defect detection systems 10. Glass sheets 14 are transported by a conveyance system 12 along an IG unit assembly line at speeds of up to 2 m/sec or more. The direction of transport of the glass sheet 14 by the conveyance system 12 is shown in FIG. 1 from right to left. The encoding device 18 tracks the location of the glass sheet 14 along the conveyance system 12. The encoding device 18 transmits a signal to the trigger circuit 20. The trigger circuit 20 receives the signal from the encoding device 18 and transmits a signal to the camera 22. The trigger circuit 20 triggers the cameras 22 to capture an image every 83.44 mm of movement of the conveyance system 12 or every 387 pixels in the field of view 23 of the camera 22.

The conveyance system 12 transports a glass sheet 14, from right to left in FIG. 1, and the glass sheet 14 first passes in the light path of a sensor 16. The sensor 16 sends a signal to the image processing system 26, the sample profile, indicating whether the glass sheet 14 has a coating 15 and if so what type of coating 15 is present on the glass sheet 14. The image processing system 26 transmits a signal to the camera 22 adjusting the "camera settings." If the output signal from the sensor 16 indicates that the glass sheet 14 does not have a coating 15, the image processing system 26 transmits a signal to the camera 22 to set the shutter speed to be 0.0007 seconds and signal gain to be −3.0 dB and gamma to be 3.5. If the output signal from the sensor 16 indicates that the glass sheet 14 has a coating 15, the image processing system 26 transmits a signal to the camera 22 to set the shutter speed to be 0.0008 seconds and the signal gain to be 1.5 dB and gamma to be 1.0.

The camera 22 and the illumination system 24 are enclosed in housing 11. The housing 11 reduces the amount of stray light that may be directed at the glass sheet 14 from the room during the inspection process. The housing 11 also provides physical protection from other elements in the production environment. The camera 22 captures images of the glass sheet 14 every 83.44 mm of movement of the conveyance system 12 or every 387 pixels in the field of view of the camera 22. These images captured by the camera 22 are transmitted to the image processing system 26. Standard image processing techniques including those embodied in software from Open Source Computer Vision are used. Image processing uses absolute or adaptive intensity thresholding. Standard blob analysis generates measurements including length, width, ratio of perimeter to area and Euler number. The images are then output to the image display 28.

Figure 2:
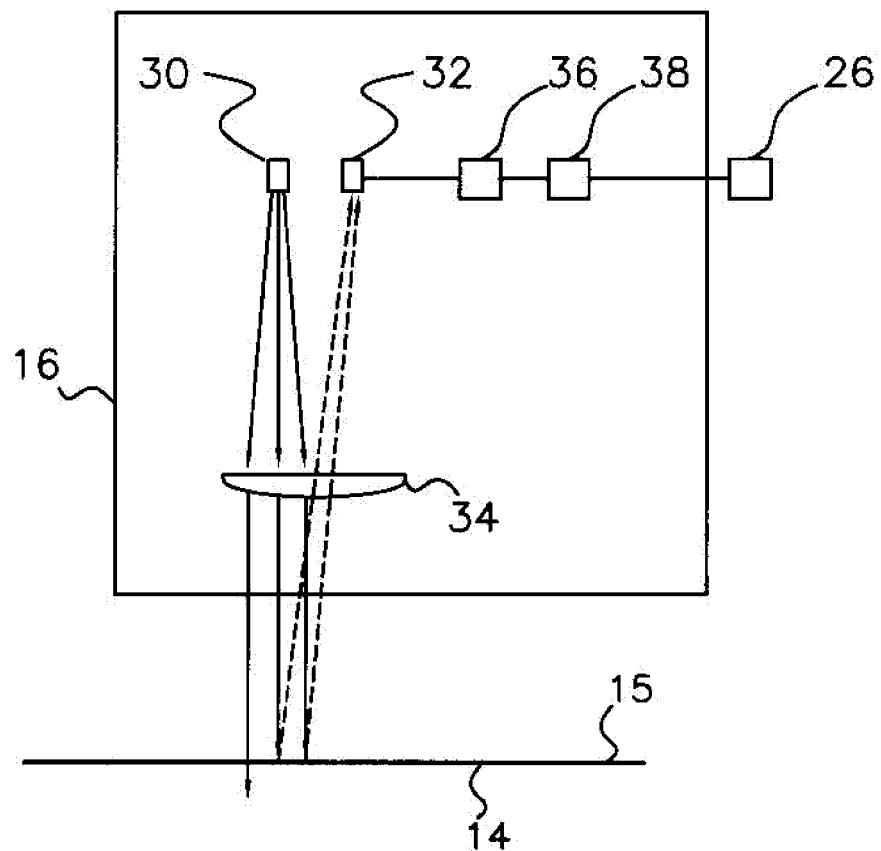
FIG. 2 shows a schematic of the coating sensor.

FIG. 2 illustrates a schematic view of the sensor 16. The sensor 16 is comprised of an emitter 30, a receiver 32, a lens 34, a bandpass filter 36 and an embedded microprocessor 38. The LED emitter 30 of sensor 16 projects light of approximately 940 nm. This light is partially collimated by passing through the lens 34 and onto the glass sheet 14. The receiver 32 is a photodiode receiver and detects the light reflected from the glass sheet 14. The IR energy received by the receiver 32 is filtered via a bandpass filter 36 to remove ambient IR noise, leaving the signal portion. The signal is converted from analog to digital, and passed to the embedded microprocessor 38 which compares it to threshold values, that have been established empirically by measurement, for empty space, clear glass, and various coated glasses. The embedded microprocessor outputs a sample profile to the image processing system 26, indicating whether a glass sheet 14 with a coating 15 or a glass sheet 14 without a coating 15 is to be examined by the optical inspection system.

Figure 3:
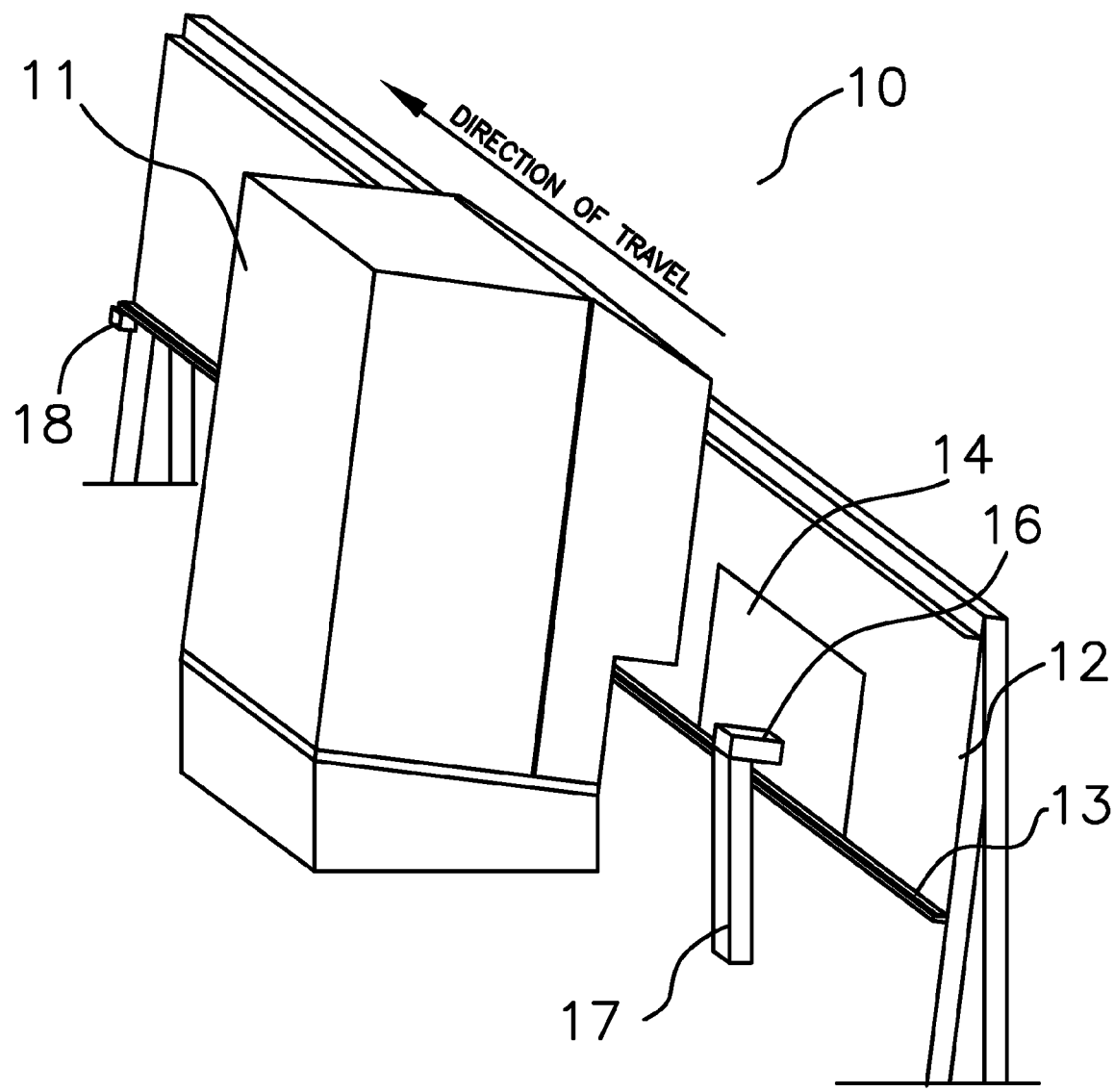
FIG. 3 shows an isometric view of the glass defect detection system.

FIG. 3 illustrates an isometric view of the conveyance system 12. The belt 13 of the conveyance system 12 moves the glass sheet 14 from right to left as shown in FIG. 3. The glass sheet 14 first passes between the sensor 16 and the conveyance system 12. The sensor 16 is attached to a sensor support 17 so that the sensor 16 is in line with the glass sheet 14. The sensor 16 transmits a signal with a sample profile indicating which coating 15 is present on the glass sheet 14 to the image processing system 26. The glass sheet 14 next passes between the conveyance system 12 and the housing 11. The housing 11 encloses the camera 22 and the illumination system 24. The housing 11 may be constructed of sheet steel or other material which can protect the camera 22 and illumination system 24 from stray light and other physical harm in the glass production environment. The encoding device 18 allows the precise tracking of the location of the glass sheets 14 along the conveyance system 12. The encoding device 18 may be a rotary encoder which pulses 2540 times per revolution of a shaft driving the belt 13 of the conveyance system 12. The encoding device 18 may be like those manufactured by Dynapar. The encoding device 18 tracks the position of the glass sheet 14. The encoding device 18 transmits a signal to the trigger circuit 20 as shown in FIG. 1.

FIG. 4 illustrates a plot of the reflectance as a function of wavelength from 300 nm to 2000 nm for a glass sheet 14 without a coating 15 and four glass sheets 14 with four distinct coatings 15, A, B, C and D. The reflectance presented in FIG. 4 is that detected by the sensor 16. The glass sheets 14 with low emissivity coatings 15 all have a greater reflectivity than a glass sheet 14 without a coating 15 from 730 nm to 2000 nm as shown in FIG. 4. Three of the four low emissivity coatings 15 have a greater reflectivity than a glass sheet 14 without a coating 15 from 300 to 335 nm as shown in FIG. 4.

Figure 5:
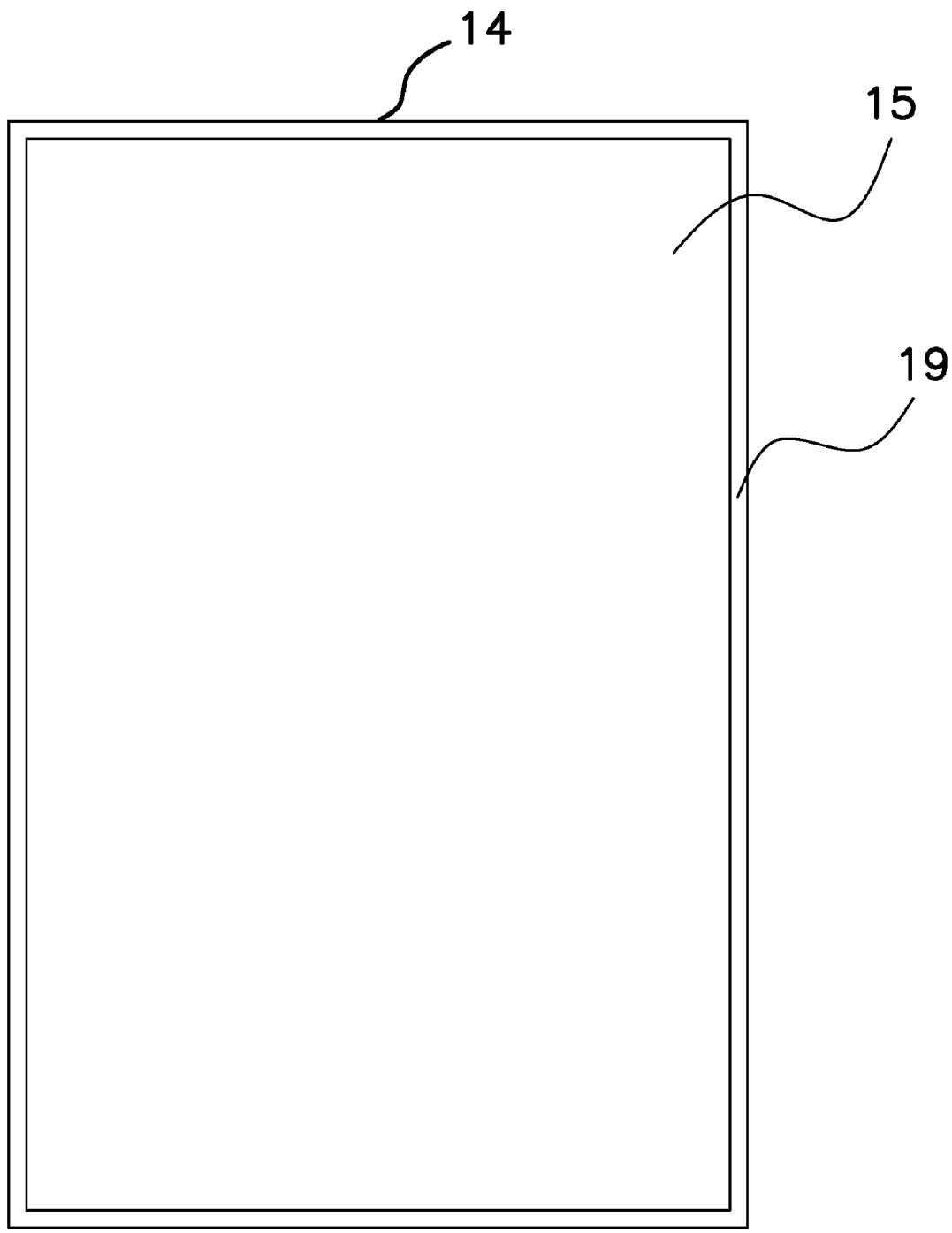
FIG. 5 shows a front view of the surface of a coated glass sheet.

FIG. 5 illustrates a glass sheet 14 with a coating 15 on a first surface of the glass sheet 14 and an edge deleted perimeter 19 of the coating 15 on the first surface. The coating 15 is removed from the perimeter of the glass sheet 14 by grinding to create the edge deleted perimeter 19. The width of the edge deleted perimeter 19 is generally less than one inch and may be 0.375-inch plus 0.06-inch. The geometry of the edge deleted perimeter 19 is a frame with a width of about 0.375-inch plus 0.06-inch. The proper geometry of the edge deleted perimeter 19 is that of a regular frame with no coating 15 remaining on the edge deleted perimeter 19 following grinding. The edge deleted perimeter 19 may have other shapes including the removal of the coating 15 from only the two long sides of rectangular glass sheets 14 or the removal of the coating 15 only from the two shorter sides of the rectangular glass sheets 14.

To use a glass defect detection system 10 in accordance with the present invention to inspect a glass sheet 14, the glass defect detection system 10 may be installed on an IG production line. When installed on an IG production line, the glass defect detection system 10 is integrated into the conveyance system 12 of the line. The glass defect detection system 10 could be installed on production and inspection lines for other transparent sheets including mirrored glass, acrylic, polycarbonate and other optically transparent polymer sheets.

The method according to the present invention for the examination of a glass sheet 14 for the purpose of detecting defects in and on the glass sheet 14 comprises: detecting a coating 15 on the glass sheet 14 with a sensor 16, setting a sample profile for an optical inspection system based on a coating measurement from the sensor 16, transmitting the sample profile to an image processing system 26, changing inspection variables in response to the sample profile, illuminating the glass sheet 14 with light from the illumination system 24 using inspection variables, capturing the light with an imaging device such as a camera 22 using inspection variables, transmitting an image received by the imaging device to an image processing system 26, analyzing the image for defects using inspection variables and using the results of analyzing the image for defects to accept or reject the glass sheet 14.

As the glass sheet 14 moves along the conveyance system 12, the sensor 16 detects the presence or absence of the coating 15 and the characteristics of the coating 15, if present, on the glass sheet 14. The sensor 16 is comprised of an emitter 30, an LED, and a receiver 32, an infrared sensitive photodiode, with the emitter 30 emitting at 940 nm and the receiver receiving at 940 nm. Wavelengths in the near IR (800 to 1200 nm) or in the near ultraviolet (200-320 nm) may also be used with this invention. The infrared energy received by the receiver 32 is filtered by bandpass filter 36 and the remaining signal is converted from an analog signal to a digital signal and passed to an embedded microprocessor 38. The embedded microprocessor 38 outputs threshold values indicating which of a plurality of coatings 15 on glass sheets 14 has been detected and the characteristics of the coatings 15, or sample profile.

As the glass sheet 14 moves along the conveyance system 12, the illumination system 24 directs light at the glass sheets 14 using Lumiled LED lights of 460-540 nm wavelength. A lens 25 may be used to focus the light into a semi-collimated beam. Various illumination systems 24 may be used with this invention including the use of bright field lighting, dark field lighting or a combination of bright field and dark field lighting. Reflected light or transmitted light may also be used with this invention.

As the glass sheet 14 moves along the conveyance system 12 and passes between the conveyance system 12 and the illumination system 24, the camera 22 captures images of the light reflected by the glass sheet 14. It is also possible with this invention for the camera 22 to capture images of transmitted light from the glass sheet 14. A Point Gray Research area scan camera with a field of view 23 of 1600×1200 pixels is used with this invention. The camera 22 may be an area scan image device, a line scan image device or may utilize CMOS, CCD or other image sensors. Other area scan, line scan, CMOS and CCD image sensors with different sized fields of view 23 or from different manufacturers may be used with this invention.

The field of the view 23 of the camera 22 may be divided into two areas. The first half of the field of view 23 may detect bright field lighting and second half of the field of view 23 may detect dark field lighting.

The images obtained by the camera 22 are transmitted to the image processing system 26. The image processing system 26 uses standard image processing techniques available in software from Open Source Computer Vision Library. Other image processing techniques may be used with this invention. The image processing system 26 outputs images to the image display 28.

As the glass sheet 14 moves along the conveyance system 12, the encoding device 18 tracks the position of the glass sheet 14. The encoding device 18 is a rotary encoder which pulses 2540 times per revolution of the shaft driving the belt 13 of the conveyance system 12 and is manufactured by Dynapar. Other devices for tracking the position of glass sheets 14 along a conveyance system 12 may be used with this invention.

As the glass sheet 14 moves along the conveyance system 12, the encoding device 18 transmits a signal to the trigger circuit 20, triggering the optical inspection system by transmitting a signal to the camera 22. The trigger circuit 20 triggers the camera 22 to capture an image every 83.4 mm of movement of the conveyance system 12 or every 387 pixels in the field of view 23 of the camera 22. Other conveyance system 12 distances or pixel dimensions of the field of view 23 may be used with this invention.

The foregoing discussion discloses and describes merely exemplary embodiments of the present invention. The invention is not limited to the method and the apparatus for inspection as described in the detail above. Upon review of the specification, one skilled in the art will readily recognize from such discussion, and from the accompanying drawings and claims, that various changes, modifications and variations can be made therein without departing from the spirit and scope of the invention as defined in the following claims.

What is claimed is:

1. An apparatus for the inspection of a transparent sheet for the purpose of detecting defects in and on the transparent sheet, comprising:
   a sensor for detecting a transparent light reflective coating on the transparent sheet;
   a sample profile defined by the sensor for the coating;
   inspection variables which correspond to the sample profile;
   an optical inspection system, which uses the inspection variables, and comprising:
      an illumination system for projecting light onto the transparent sheet;
      an imaging device for receiving light and transmitting an image of the transparent sheet, and;
      an image processing system for receiving the image of the transparent sheet from the imaging device and analyzing the image for defects.

2. An apparatus, as in claim 1, wherein the transparent sheet is glass.

3. An apparatus, as in claim 1, wherein the transparent sheet is glass with a light reflective coating.

4. An apparatus, as in claim 3, wherein the coating has optical quality defects which are detected.

5. An apparatus, as in claim 3, wherein the coating has an edge deleted perimeter.

6. An apparatus, as in claim 5, wherein the edge deleted perimeter is absent.

7. An apparatus, as in claim 5, wherein the edge deleted perimeter is not of the proper geometry.

8. An apparatus, as in claim 1, wherein the transparent sheet is a high transmissivity polymer.

9. An apparatus, as in claim 1, wherein the transparent sheet is acrylic.

10. An apparatus, as in claim 1, wherein the transparent sheet is polycarbonate.

11. A method for the examination of a transparent sheet for the purpose of detecting defects in and on the transparent sheet comprising:
    detecting a light reflective coating on the transparent sheet with a sensor,
    setting a sample profile based on a coating measurement from the sensor,
    changing inspection variables in response to the sample profile, using the inspection variables in an optical inspection system, illuminating the transparent sheet with light from an illumination system, capturing the light with an imaging device, transmitting an image of the transparent sheet received by the imaging device to an image processing system, analyzing the image for defects, and using the results of analyzing the image for defects to accept or reject the transparent sheet.

12. A method, as in claim 11, wherein the transparent sheet is glass.

13. A method, as in claim 11, wherein the transparent sheet is glass with a light reflective coating.

14. A method, as in claim 13, wherein the coating has optical quality defects which are detected.

15. A method, as in claim 13, wherein the coating has an edge deleted perimeter.

16. A method, as in claim 13, wherein the edge deleted perimeter is absent.

17. A method, as in claim 13, wherein the edge deleted perimeter is not of the proper geometry.

18. A method, as in claim 11, wherein the transparent sheet is a high transmission polymer.

19. A method, as in claim 11, wherein the transparent sheet is acrylic.

20. A method, as in claim 11, wherein the transparent sheet is polycarbonate.

21. An apparatus for the examination of a sheet of flat glass on an insulated glass unit assembly line for the purpose of detecting defects in and on the flat glass, comprising:

a sensor for detecting a transparent light reflective coating on the flat glass;

a sample profile defined by the sensor for the coating;

inspection variables which correspond to the sample profile;

an optical inspection system, which uses inspection variables, and comprising:

an illumination system for projecting light onto the flat glass;

an imaging device for receiving light and transmitting an image of the flat glass, and;

an image processing system for receiving the image of the flat glass from the imaging device and analyzing the image for defects.

* * * * *